(12) United States Patent
Cruikshank et al.

(10) Patent No.: US 8,398,973 B2
(45) Date of Patent: Mar. 19, 2013

(54) METHODS AND COMPOSITIONS FOR PREVENTING ADHESION

(75) Inventors: William W. Cruikshank, Westford, MA (US); David M. Center, Wellesley Hills, MA (US)

(73) Assignee: Trustees of Boston University, Boston, MA (US)

(*) Notice: Subject to any disclaimer, the term of this patent is extended or adjusted under 35 U.S.C. 154(b) by 0 days.

(21) Appl. No.: 12/988,145

(22) PCT Filed: Apr. 16, 2009

(86) PCT No.: PCT/US2009/040779
§ 371 (c)(1),
(2), (4) Date: Oct. 15, 2010

(87) PCT Pub. No.: WO2009/129374
PCT Pub. Date: Oct. 22, 2009

(65) Prior Publication Data
US 2011/0123526 A1    May 26, 2011

Related U.S. Application Data

(60) Provisional application No. 61/124,615, filed on Apr. 18, 2008.

(51) Int. Cl.
*A61K 39/395* (2006.01)

(52) U.S. Cl. ............... 424/130.1; 424/133.1; 424/139.1

(58) Field of Classification Search .................. None
See application file for complete search history.

(56) References Cited

U.S. PATENT DOCUMENTS

| 5,530,101 | A  | * | 6/1996 | Queen et al. ............ 530/387.3 |
| 6,699,466 | B1 | * | 3/2004 | Center et al. .............. 424/85.2 |
| 7,208,149 | B2 |   | 4/2007 | Center et al. |

OTHER PUBLICATIONS

Chuntharapai et al (1997), Methods in Enzymology, vol. 288, pp. 15-27.*
Tzianabos, A.O. et al., "Functional Th1 Cells are Required for Surgical Adhesion Formation in a Murine Model" The Journal of Immunology (2008)pp. 6970-6976, vol. 180.

* cited by examiner

*Primary Examiner* — Prema Mertz
(74) *Attorney, Agent, or Firm* — Scully, Scott, Murphy & Presser, P.C.

(57) ABSTRACT

This invention provides methods and compositions for preventing post-surgical adhesion formation based on use of an interleukin-16 (IL-16) antagonist, including an IL-16 antagonist peptide and/or an IL-16 antagonist antibody.

9 Claims, 2 Drawing Sheets

METHODS AND COMPOSITIONS FOR PREVENTING ADHESION

STATEMENT REGARDING FEDERALLY SPONSORED RESEARCH OR DEVELOPMENT

This invention was made with Government Support under Contract Nos. HL32802 and AI35680 by the National Institutes of Health. The Government has certain rights in this invention.

FIELD OF THE INVENTION

This invention relates to prevention and inhibition of adhesion formation. In particular, this invention relates to methods and compositions for preventing adhesion formation based on use of an interleukin-16 (IL-16) antagonist.

BACKGROUND OF THE INVENTION

Tissue trauma in the peritoneal and pelvic cavities following surgery or bacterial infection results in adhesions that are a debilitating cause of intestinal obstruction, chronic pelvic pain, and infertility in women. During the response to surgical trauma, unchecked fibrosis leads to the development of fibrous adhesions that bind apposing tissues together in an inappropriate manner. Surgical adhesions are a major complication of gynecologic and abdominal surgery, with an incidence as high as 50-90% (Trimbos-Kemper et al., *Fertil Steril* 43:395-400 (1985); Monk et al., *Am. J. Obstet. Gynecol.* 170:1396-1403 (1994); Lower et al., *Brit. J. Obstet. Gynaecol.* 107:855-862 (2000)). Adhesions that develop after gynecologic surgery are a source of chronic pelvic pain and infertility (Lower et al. (2000)). In addition, most severe adhesions in the abdominal cavity can cause potentially fatal small bowel obstruction and organ failure (Ellis, *Eur. J. Surg. Suppl.* 577: 5-9 (1997); Wilson et al., *Br. J. Surg.* 85:1294-1298 (1998); Diamond et al., *Hum. Reprod. Update* 7:567-576 (2001).

Adhesion generally occurs as a result of the normal wound healing response within days after injury. The molecular and cellular mechanisms involved in the development of adhesions are not fully understood. It has been reported that Th1 CD4$^+$ T cells were critical to adhesion formation and orchestrate host response after peritoneal injury (Chung et al., *J. Exp. Med.* 195:1471-1478 (2002)).

Current treatments to prevent or reduce the severity of adhesions rely primarily on the use of barrier devices or bioresorbable gels. However, effective adhesion reduction by physical barriers may be limited to the site of application (*J. Gastrointest Surg* 13:35-42, 2009). Anti-inflammatory drugs such as corticosteroids and non-steroids, and protease inhibitors, have also been utilized in adhesion prevention (*Clin. Exp. Gynecol.* 28: 126-127, 2001; US Publication 2006/0122101A1). However, systemic or intraperitoneal administration of corticosteroids, while reducing adhesion formation, also severely compromises wound healing and causes immunosuppression in post-surgical patients.

There remains a need for an effective approach to prevent and inhibit formation of adhesion.

SUMMARY OF THE INVENTION

The present invention is premised on the discovery that IL-16 antagonists can prevent or reduce formation of adhesion. Accordingly, the present invention provides methods and compositions for preventing or reducing formation of adhesion based on use of an IL-16 antagonist.

In one aspect, the invention is directed to a method of preventing or reducing post-surgical adhesion in a mammalian subject by administering an IL-16 antagonist to the subject before, during or after the surgery.

In certain embodiments, the present method is based on administration of an IL-16 antagonist that is an anti-IL-16 antibody.

In one preferred embodiment, the antibody is directed to, i.e., specifically recognizes and binds to, an epitope or a peptide fragment which includes the RR or KR motif, or an epitope or a peptide fragment that is sufficiently close to the RR or KR motif in the C-terminal region of a native IL-16.

In another preferred embodiment, the antibody is a human or humanized antibody suitable for administration to a human subject.

In other embodiments, the present method is based on administration of an IL-16 antagonist that is an IL-16 antagonist peptide.

In one embodiment, the IL-16 antagonist peptide is a fragment of a native mammalian IL-16 which contains the RR or KR motif and is at least 4 amino acids in length. In preferred embodiments, IL-16 antagonist peptides contain the RR or KR motif and are at least 6 amino acids, preferably at least 8 amino acids, or at least 16 amino acids in length. The peptides generally are not more than 35 amino acids in length.

In another aspect, the present invention provides a medicament or composition prepared to contain an IL-16 antagonist, in combination with another agent or barrier material that inhibits formation of adhesion.

DETAILED DESCRIPTION OF THE INVENTION

Figure 1:
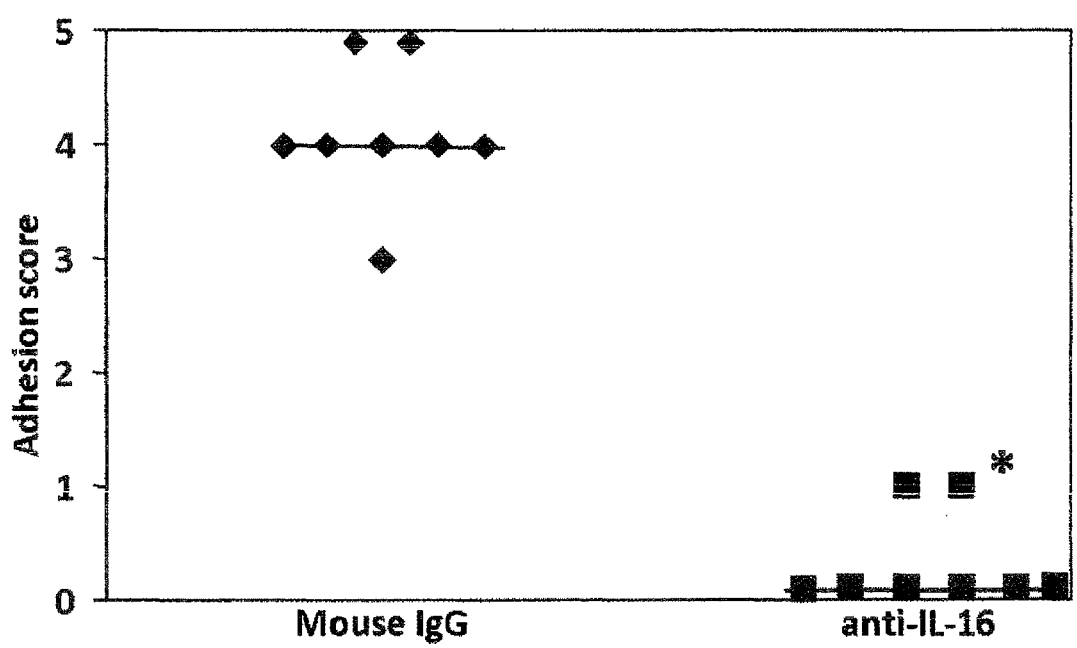
FIG. 1. Sixteen C57BL/6 mice were subjected to cecal abrasion surgery and treated with 100 μg of either anti-IL-16 or control antibody, 6 h, 24 h, 3 d and 5 d after surgery. Six days after surgery the mice were euthanized and scored for adhesions. *, P=0.0022, Mann-Whitney U test. The bars indicate the median adhesion score.

It has been identified in accordance with the present invention that an IL-16 antagonist can prevent or reduce formation of adhesion. Accordingly, the present invention provides methods and compositions for preventing or reducing formation of adhesion based on use of an IL-16 antagonist.

The methods and compositions of the present invention can be used to treat, prevent or inhibit adhesions, including particularly post-surgical adhesions in a subject, which can form as a result of abdominal, gynecological, cosmetic, reconstructive, orthopedic, cardiac, or spinal surgeries or procedures. The methods and compositions of the present invention can also be used to treat or reduce severity of adhesions formed in cases other than surgical procedures, such as cases of injury or inflammatory visceral adhesion.

By "treating", "reducing" or "inhibiting" adhesions, it is meant that formation of adhesion is completely or partially prevented or eliminated, or the severity or extent of adhesion is reduced.

The term "subject" means any mammalian subject, including a human, murine, canine, feline, monkey subject, as well as horse and cattle.

IL-16 Antagonist

The term "IL-16 antagonist" as used herein means any molecule that completely or substantially inhibits, suppresses or causes the cessation of at least one IL-16-mediated biological activity by, e.g., interfering with, blocking or otherwise preventing the interaction or binding of IL-16 to an IL-16 receptor, e.g., the CD4 receptor. By "substantially" it is meant that an antagonist can reduce an IL-16 mediated activity by at least 40%, 50%, 60%, 75%, 85%, 90% or even 95% or greater.

"An IL-16-mediated biological activity" as used herein includes chemotaxis of CD4+ cells such as CD4+ T cells, inhibition of retroviral replication (such as inhibition of HIV and SIv in infected PBMCs), upregulation of IL-2R on CD4+ T cells, synergy with IL-2 for $CD4^+$ T cell proliferation, induction of RAG-1 and RAG-2 expression in $CD4^+$ pro-B cells, and inhibition of Mixed Lymphocyte Reaction (MLR). These IL-16 mediated biological activities can be determined using readily available assays described by, for example, Cruikshank et al. (*Proc. Natl. Acad. Sci. USA* 91: 5109-5113, 1994); Maciaszek et al. (*J. Immunol.* 158:5, 1997), Zhou, et al. (*Nature Medicine* 3:659, 1997), Baier et al. (*Nature* 378: 563, 1995); Parada et al. (*J. Immunol.* 160:2115, 1998); Szabo et al. (*J. Immunol.*, 161:2248, 1998); or Theodore et al. (*J. Immunol.* 157:1958, 1996).

An IL-16 antagonist can function in two ways to antagonize the function of IL-16. The antagonist can compete with IL-16 for the cell surface receptor thereby interfering with, blocking or otherwise preventing the binding of IL-16 to an IL-16 receptor. This type of antagonist, i.e., which binds the receptor but does not trigger signal transduction, is also referred to herein as a "competitive antagonist". Alternatively, an IL-16 antagonist can bind to or sequester IL-16 with sufficient affinity and specificity to substantially interfere with, block or otherwise prevent binding of IL-16 to an IL-16 receptor, thereby inhibiting, suppressing or causing the cessation of at least one IL-16-mediated biological activity, such as T-cell chemotaxis, for example.

According to the present invention, IL-16 antagonists suitable for practice of the present invention include antibodies that specifically bind to IL-16 and neutralize one or more IL-16-mediated activities (also referred to as "IL-16 antagonist antibodies" or "neutralizing antibodies"). IL-16 antagonists suitable for use in the present invention also include peptides (or "IL-16 antagonist peptides").

IL-16 Antagonistic Antibodies

IL-16 antagonist antibodies have been described in the art, including mAb14.1 and mAb 17.1 (see, Hessel et al., *J. Immunol.* 160: 2998-3005, 1998, and Keane et al., *J. Immunol.* 160: 5945-5954, 1998), as well as antibodies described in U.S. Pat. No. 7,208,149, all of which are suitable for use in the present invention of preventing adhesion.

In a preferred embodiment, neutralizing antibodies are directed to epitopes within the C-terminal region of a native IL-16 molecule. It has been documented that the Arg/Lys-Arg motif, i.e., $R^{106}$-$R^{107}$ of human IL-16, $R^{103}$-$R^{104}$ of murine IL-16 or $K^{106}$-$R^{107}$ of IL-16 from squirrel monkey and *Aotus trivirgatus*, in the C-terminal region of IL-16, is critical to CD4 receptor binding and activation by IL-16, and to IL-16 mediated chemoattractant activity. See, e.g., U.S. Pat. No. 7,208,149. Therefore, antibodies that bind to an epitope or a peptide fragment which includes the RR or KR motif, or an epitope or peptide fragment that is sufficiently close to the RR or KR motif, are believed to have the ability to block or inhibit the function of the RR motif that is required for interacting with an IL-16 receptor, thereby blocking and neutralizing at least one IL-16-mediated biological activity for IL-16-mediated activities.

The term "epitope" is well understood in the art and refers to a molecular region or structural determinant on the surface of an antigen capable of binding to an antibody and eliciting an immune response. An epitope can be constituted by contiguous or non-contiguous amino acids. By "sufficiently close", it is meant that an epitope, defined by a linear contiguous peptide fragment of IL-16 as an convenient example, is within 30 amino acids of the RR or KR motif, or preferably within 25 amino acids, 20 amino acids, 15 amino acids, 10 amino acids, and more preferably within 5, 4, 3, 2 amino acids or only 1 amino acid of the RR or KR motif.

In one embodiment, the antibodies are directed towards a peptide fragment of the C-terminal region of a native mammalian IL-16 molecule. In a specific embodiment, the peptide fragment includes 30 amino acids, or 25 amino acids, or 20 amino acids, or 16 amino acids, or 15 or fewer, or 10, 9, 8, or 7 amino acids, from the C-terminal region of a native mammalian IL-16 molecule. In one embodiment, the peptide fragment includes the last (C-terminal) 30 amino acids, or 25 amino acids, or 20 amino acids, or 16 amino acids, or 15 or fewer, or 10, 9, 8, or 7 amino acids, of a native mammalian IL-16 molecule. In another embodiment, the peptide fragment includes the RR or KR motif and consists of 30 amino acids, or 25 amino acids, or 20 amino acids, or 16 amino acids, or 15 or fewer amino acids, or 10, 9, 8, or 7 amino acids, of a native mammalian IL-16 molecule.

The antibodies of the present invention can be generated by well-known methods. For example, an IL-16 protein or a polypeptide or peptide fragment thereof, in combination with Freund's adjuvant, can be injected into an appropriate animal such as rabbit, mice, cow, guinea pig, rat, donkey and the like. When small IL-16 peptides are used as antigen, such peptides can be coupled to a carrier polypeptide, e.g., KLH, prior to immunization as described in Ausubel et al. (1989) *Current Protocols in Molecular Biology*, John Wiley & Sons, New York.

Both polyclonal antibodies and monoclonal antibodies can be prepared using the immunized animal. The procedure for making polyclonal and monoclonal antibodies is well known in the art and can be found in, e.g., Harlow, E. and Lane, D., *Antibodies: A Laboratory Manual*, Cold Spring Harbor Press, 1988. Polyclonal antibodies can be readily purified from the serum of the immunized animal using a number of well known protein purification procedures such as affinity chromatography. Monoclonal antibodies can be prepared by following the standard hybridoma techniques (see e.g. Kohler et al., *Nature* 256:495, 1975). Briefly, the spleens of the immunized animal can be removed, and their lymphocytes fused to an immortal cell line. The resulting hybridomas can be screened initially by binding affinity to the relevant peptide antigen, which can be determined by various immuno assays such as ELISA.

Functional derivatives of the identified antibodies are also contemplated. "Functional derivatives" refer to antibody molecules or fragments that are derived from an originally identified IL-16 antagonistic antibody and that have retained the antigen specificity of the original antibody. Examples of functional derivatives include Fab, Fab', F(ab')$_2$ of an original antibody, single chain antibodies, deimmunized antibodies such as humanized antibodies, and the like.

Deimmunized antibodies refer to antibodies derived from an original antibody, where the original antibody has been modified to reduce immunogenicity to an intended recipient.

For example, for preventing adhesion formation in humans, anti-IL-16 antibodies raised in a non-human animal can be "humanized" to reduce the immunogenicity the antibodies to human recipients. For example, to humanize a monoclonal antibody raised in mice, one approach is to make mouse-human chimeric antibodies having the original variable region of the murine mAb, joined to constant regions of a human immunoglobulin. Chimeric antibodies and methods for their production are known in the art. See, e.g., Cabilly et al., European Patent Application 125023 (published Nov. 14, 1984); Taniguchi et at, European patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Robinson et al., International Patent Publication PCT/US86/02269 (published 7 May 1987); Liu et al., *Proc. Natl. Acad. Sci. USA* 84:3439-3443 (1987); Sun et al., *Proc. Natl. Acad. Sci. USA* 84:214-218 (1987); Better et al., *Science* 240:1041-1043 (1988). These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes. Humanized antibodies can be made using a second approach, i.e., to construct a reshaped human antibody, as described in Queen et al., *PNAS* 86:10029-10033 (1988); Riechmann et al., *Nature* 332:323-327 (1988). It is known that the heavy and light chains of an antibody molecule each contribute three CDRs to the antigen binding region of the antibody molecule. Humanization of an antibody molecule can be achieved by transferring the six CDRs from the antibody molecule (donor framework region) to an acceptor framework region of a human antibody molecule, while retaining the specificity of antigen binding.

Alternatively, and more preferably, fully human anti-IL-16 antibodies can be generated and are used for treating adhesions in humans. Fully human anti-IL-16 antibodies can be generated by immunizing a mouse reconstituted with a human immune system with an IL-16 protein or a fragment thereof. Mice reconstituted with a human immune system, or "humanized mice", have been described in the art, e.g., Pearspn et al., *Current Protocols Immunolgoy*, Supplement 81, 15.21.1-15.21.21 (2008); Giassi et al., *Exp. Biol. Med.* 233: 997-1012 (2008); Shultz et al., *Nat Rev Immunol* 7:118-30 (2007); and Melkus et al., *Nature Medicine* 12, 1316-1322 (2006). Generally speaking, such humanized mice are created by engrafting immunodeficient mice with hematopoietic stem cells or peripheral blood mononuclear cells from humans. Human B cells are then isolated from the humanized mice that have been immunized with IL-16 or an IL-16 peptide, and fused with an immortalized cell to produce a hybridoma cell that synthesizes and secretes a human anti-IL-16 antibody.

Fully human or humanized anti-IL-16 antibodies can also be generated by immunizing a non-human animal that has been genetically engineered to contain one or more human or humanized immunoglobulin loci which are capable of undergoing gene rearrangement and gene conversion in the transgenic non-human animal to produce diversified human or humanized immunoglobulins. Non-human animals genetically engineered to contain one or more human or humanized immunoglobulin loci to produce diversified human or humanized immunoglobulins have been described by, e.g., by Bruggemann et al. *Curr Opin Biotechnol* 8(4): 455-8 (1997); Lonberg et al. *Int Rev Immunol* 13(1):65-93 (1995); Neuberger et al., *Nature* 338: 350-2 (1989), and U.S. Publication 20030017534A1.

Antibodies raised that specifically bind to relevant antigens or immunogens can be further screened for neutralization activity, i.e., the ability of inhibiting at least one IL-16 mediated biological activity, as defined above, such as chemotaxis of CD4+ T cells.

IL-16 Antagonistic Peptides

IL-16 antagonistic peptides, i.e., peptides derived from IL-16 that antagonize one or more activities of IL-16, are suitable for use in the present invention and have been described in the art. See, e.g., U.S. Pat. No. 7,208,149, the disclosure of which is incorporated herein by reference.

In one embodiment, an IL-16 antagonist peptide suitable for use in the present invention is at least 4 amino acids in length and substantially corresponds to the C-terminal sequence of a native mammalian IL-16 molecule surrounding the RR or KR motif, e.g., $R^{106}$-$R^{107}$ of human IL-16, $R^{103}$-$R^{104}$ of murine IL-16, or $K^{106}$-$R^{107}$ of IL-16 from squirrel monkey and *Aotus trivirgatus*. The numbering of the amino acids is defined in accordance with the sequences of the mature, secreted form of IL-16. The sequences of the mature IL-16 from human and mouse have been described by Keane et al. (*J. Immunol* 160: 5945-5954, 1998) and are set forth herein as SEQ ID NOS: 1-2, respectively. The sequences of the full-length pro-IL-16 from African green monkey, rhesus monkey, mangeby, zebu, macaque, squirrel monkey and *Aotus trivirgatus* have been published by the Genbank database.

By "substantially corresponds to" it is meant to include peptides having sequences that are identical to the native sequences of the C-terminal region of human or murine IL-16 surrounding the RR or KR motif, as well as homologs and analogs of such peptides.

By "homologs" and "analogs" it is meant to include derivatives of peptides which differ by one or more amino acid alterations, e.g., substitutions (conservative or non-conservative, but preferably conservative substitutions), additions or deletions of amino acid residues, or side chain modifications, which do not abolish the IL-16 antagonist properties of the relevant peptides.

Preferred homologs of a peptide include those that shares a degree of identity with the relevant peptide of at least 75%, at least 85%, or at least 90%, or even 95% or greater.

The phrase "analog" also includes the use of chemically derivatized residues in place of a non-derivatized residue as long as the peptide retains the requisite IL-16 antagonist properties.

Analogs also include addition of amino acids to the N-terminus or C-terminus of a relevant peptide. For example, the addition of cysteine to the N- or C-terminus of a peptide, by which, if desired, the peptide can be covalently attached to a carrier molecule, e.g., albumin or PEG (polyethylene glycol). Such attachment, it is believed, can minimize clearing or achieve a desirable clearance rate of the peptide from the blood and also prevent proteolysis of the peptides.

In addition, for purposes of the present invention, peptides containing D-amino acids in place of L-amino acids are also included in the term "analogs". The presence of such D-isomers may help minimize proteolytic activity and achieve a desirable clearance rate of the peptide.

In one embodiment, the IL-16 antagonist peptide is a fragment of a native mammalian IL-16 which contains the RR or KR motif and is at least 4 amino acids in length. It has been found that IL-16 peptides as short as 4 amino acids in length and containing the RR or KR motif can inhibit the activities of IL-16.

In a specific embodiment, the IL-16 antagonist peptides for use in preventing adhesion are fragments of the C-terminal region of a native mammalian IL-16 molecule. For example, the peptides include the RR or KR motif and consist of at least 4 amino acids, or at least 6 amino acids, or at least 7, 8, 9, 10, 11, 12, 13, 14, 15 or 16 amino acids, or at least 20 amino acids, or at least 24 or 30 amino acids, of the C-terminal region of a native mammalian IL-16 molecule. In certain specific embodiments, the peptides are not more than 35 amino acids in length, or not more than 25, or 16, 15 or 12 amino acids.

Examples of IL-16 antagonist peptides suitable for use in preventing adhesion in a mammalian subject include those described in U.S. Pat. No. 7,208,149, particularly RRKS (SEQ ID NO: 3), RRTS (SEQ ID NO: 4), KRKS (SEQ ID NO: 5), RRAS (SEQ ID NO: 6), RRKA (SEQ ID NO: 7), RRTA (SEQ ID NO:8), VIRR (SEQ ID NO: 9), VLRR (SEQ ID NO: 10), VIKR (SEQ ID NO: 11), IRRK (SEQ ID NO: 12), IRRT (SEQ ID NO: 13), LRRK (SEQ ID NO: 14), IKRK (SEQ ID NO: 15); RRTSLQ (SEQ ID NO:16), RRTSLQ (SEQ ID NO:1'7), RRKSCM (SEQ ID NO:18), KRKSMQ (SEQ ID NO: 19), RRTSLQ (SEQ ID NO: 20), RRKALQ (SEQ ID NO: 21), RRTALQ (SEQ ID NO: 22); RRKSLQSK (SEQ ID NO: 23), RRTSLQCK (SEQ ID NO: 24), RRKSLQPK (SEQ ID NO: 25), RRKSCMSK (SEQ ID NO: 26), KRKSMQSK (SEQ ID NO: 27), RRASLQSK (SEQ ID NO: 28), RRKALQSK (SEQ ID NO: 29), RRTALQCK (SEQ ID NO: 30), RRASLQCK (SEQ ID NO: 31); RRKSLQSKET-TAAGDS (SEQ ID NO: 32), RRTSLQCKQTTASADS (SEQ ID NO: 33), RRASLQSKETTAAGDS (SEQ ID NO: 34), RRKALQSKETTAAGDS (SEQ ID NO: 35), RRTALQCK-QTTASADS (SEQ ID NO: 36), and RRASLQCKQT-TASADS (SEQ ID NO: 37).

For treating adhesions in humans, it is preferable to employ IL-16 antagonist peptides having a sequence that is identical with the C-terminal region of human IL-16. Examples of such peptides include, for example, RRKS (SEQ ID NO: 3), VIRR (SEQ ID NO: 9), IRRK (SEQ ID NO: 12), RRKSLQ (SEQ ID NO: 16), RRKSLQSK (SEQ ID NO: 23), RRKSLQSKET-TAAGDS (SEQ ID NO: 32), and peptides containing any such specific human sequence.

Adhesion-Preventative Medicament or Composition

In another embodiment of the present invention, one or more IL-16 antagonists, e.g., an IL-16 antagonist antibody or peptide or a combination thereof, are included in a pharmaceutical composition or medicament formulated for use to prevent or reduce adhesions.

Such adhesion-preventative composition or medicament can also include other appropriate active ingredients, such as known anti-inflammatory agents, e.g., anti-CD4 antibodies, anti-TNFα antibodies, NSAIDS, steroids, cyclosporin-A or cytotoxic drugs; or other agents known to reduce adhesion.

The composition or medicament can also include a pharmaceutically acceptable carrier. As used herein, a "pharmaceutically acceptable carrier" includes solvents, dispersion media, isotonic agents and the like. Except insofar as any conventional media, agent, diluent or carrier is detrimental to the recipient or to the therapeutic effectiveness of the IL-16 antagonist(s) contained therein, its use in practicing the methods of the present invention is appropriate. The carrier can be liquid, semi-solid, e.g. gel or cream, or solid carriers. Examples of carriers include water, saline solutions, alcohol, gel including dydrogel, oils, lipids, liposomes, resins, porous matrices, binders, fillers, coatings, preservatives and the like, or combinations thereof.

In accordance with the present invention, the active ingredients can be combined with the carrier in any convenient and practical manner, e.g., by admixture, solution, suspension, emulsification, encapsulation, absorption and the like, and can be made in formulations such as tablets, capsules, powder, syrup, suspensions that are suitable for injections, implantations, inhalations, ingestions or the like.

In one embodiment, the active ingredients including an IL-16 antagonist are formulated in a liquid carrier for easy administration to the recipient. In another embodiment, the active ingredients are formulated into tablets or powder which can be easily stored and transported, and then readily dissolved into a liquid solution immediately prior to administration.

In still another embodiment, an IL-16 antagonist is used in conjunction with a physical barrier or bioresorbable membranes designed for use in preventing adhesion. For example, an IL-16 antagonist can be used in conjunction with a barrier material, either via incorporating into or coating the barrier material with an IL-16 antagonist, or simply by use together during a surgery. Barrier materials suitable for use together with an IL-16 antagonist include, for example, Hyskon® (dextran 70), Ringer's lactate Interceed® (oxidized regenerated cellulose), Polaxamer 407® (temperature dependent polymer), Gore-Tex® (expanded polytetrafluoroethylene), Intergel® (made of hyaluronic acid, iron, and water), and SepraFilm® (hyaluronic acid derivative film), all of which are commercially available.

Administration

The IL-16 antagonists of the present invention can be administered to a subject in need thereof in any practical and convenient manner, including by injection via a transdermal or parenteral (e.g., intravenous, intraperitoneal, intradermal, subcutaneous or intramuscular) route, or via oral administration, or spray over or apply directly into the peritoneal cavity or to a desirable tissue or organ site during a surgery before closure.

Adhesion generally forms within days of a surgery. Therefore, in accordance with the present invention, an IL-16 antagonist should be administered prior to formation of adhesion or preferably, prior to the initiation of adhesion formation, to effectively prevent or inhibit adhesion formation. Hence, an IL-16 antagonist can be given in a single dose or multiple doses to a subject immediately prior to, during, or shortly after a surgery, or any combination thereof. By "shortly after" a surgery it is meant within hours or several days from the surgery, but not more than 7 days, preferably not more than 5, 4 or 3 days from the completion of the surgery. Preferably, an IL-16 antagonist is given during a surgery, optionally followed up with administration after the surgery by way of, e.g., intravenous or intraperitoneal administration, immediately after the surgery up to 5 days, or preferably within 72 or 48 hours of the surgery. When an IL-16 antagonist peptide is employed, it may be desirable to administer the peptide during the surgery before closure, preferably by applying directly into the peritoneal cavity or the tissue or organ of injury.

Dosage

An IL-16 antagonist is administered to a subject at a "therapeutically effective amount", which means the amount required to effect an inhibition of the IL-16 activity so as to prevent completely or partially but significantly, the formation of adhesion. By "significantly" it is meant that an IL-16 antagonist can reduce the formation of adhesion by at least 50%, 75%, 85%, 90% or even 95% or greater, as compared to the formation of adhesion in the absence of the IL-16 antagonist.

Precise dosages depend on the type of formulations (a medicament containing an antagonist or a physical barrier material incorporated with an antagonist), the route of administration, the timing and frequency of the administration, the extent of injury, and the age or the recipient, for example. The precise dosage to be therapeutically effective and non-detrimental (e.g., without interfering with wound healing) can be determined by those skilled in the art including a surgeon. As a general rule, a suitable dose of an IL-16 antibody or peptide for the administration to adult humans can range from about 0.001 mg to about 20 mg per kilogram of body weight, more preferably, in the range of about 0.01 mg to about 5 mg per kilogram of body weight. The peptides should preferably be administered in an amount of at least about 50 mg per dose, more preferably in an amount up to about 500 mg per dose.

This invention is further illustrated by the following examples, which are not to be construed in any way as imposing limitations upon the scope thereof. The terms and expressions which have been employed in the present disclosure are used as terms of description and not of limitation, and there is no intention in the use of such terms and expressions of excluding any equivalents of the features shown and described or portions thereof. It is to be understood that various modifications are possible within the scope of the invention. All the publications mentioned in the present disclosure are incorporated herein by reference.

Example-1

Mouse Model of Surgical Adhesion Formation

C57BL/6J mice were purchased from The Jackson Laboratory (Bar Harbor, Me.). All animals were provided with food and water ad libitum and housed under specific pathogen-free conditions. The mice were maintained according to the Harvard Medical School animal management program, which is accredited by the American Association for the Accreditation of Laboratory Animal Care.

Abdominal surgery was performed following guidelines approved by the Harvard Medical School animal management program. Mice were anesthetized with a single injection i.p. of 0.2 ml of pentobarbital sodium (50 mg/ml; Abbott Laboratories, North Chicago, Ill.) diluted 1/5 v/v in PBS (10 mg/ml). Abdominal adhesions were induced by abrasion of the cecum and the abdominal wall as described previously (Chung et al., *J. Exp. Med.* 195:1471-1478 (2002). Briefly, sterile surgical gauze was used to abrade the cecum with 7 to 8 strokes of a consistent medium pressure. This resulted in the development of petechia on the surface of the cecum. Using this technique the resultant adhesions were predominately classified as low to moderate, according to the adhesion classification score described below. Where indicated, the degree of abrasion was modified to induce adhesions of increased severity. Severe abrasions were induced with 15 strokes of medium pressure. The procedures employed induced adhesions that were reproducible in terms of number and intensity in control animals and found to be similar in reproducibility as those obtained using a regulated mechanical device. Animals were euthanized and examined for adhesion formation 6 days later by an observer blinded to the identity of the experimental groups. The severity of adhesions in each animal was evaluated according to the following scoring system: 0, no adhesions; 1, one thin filmy adhesion; 2, more than one thin adhesion; 3, thick adhesion with focal point; 4, thick adhesion with planar attachment, or more than one thick adhesion with focal point; and 5, very thick vascularized adhesion or more than one planar adhesion. To ensure reproducibility all experiments were conducted on at least two different groups of mice on separate occasions. The median adhesion scores for the various experimental groups were compared by the Mann-Whitney U test. Differences between groups were considered significant at $P<0.05$.

Mice were injected intraperitoneally (i.p.) with 100 ug of anti-IL-16 monoclonal antibody (clone 14.1, IgG2a) or isotype control antibody (R&D Systems) at 6 h, 24 h, 3 days and 5 days following surgery. Anti-IL-16 treatment markedly reduced adhesion formation in these mice (median adhesion score of 0), compared with mice receiving a control antibody (median adhesion score of 4; P 0.0022) (FIG. 1). This data indicates that Th1 cell-generated IL-16 may function as a positive feedback mechanism for further recruitment of Th1 cells to sites of adhesion formation and that prevention of their recruitment by anti-IL-16 treatment results in reduced or completely inhibited adhesion formation.

Example-2

Rat Model of Surgical Adhesion Formation

Male Wistar rats (200-225 g; Charles River Labs, Wilmington, Mass.) housed at constant room temperature and under 12 hr light/dark cycles, were allowed access to food and water ad libitum. The protocol for animal care and operative procedures was approved by the Institutional Animal Care and Use Committee at the Boston University School of Medicine. Ischemic intraperitoneal buttons were created as follows: After induction of anesthesia, a midline incision was made and six buttons were created by grasping approximately 5 mm of peritoneal tissue with forceps and ligating the base of the tissue with 4-0 silk ligature. 1 cc normal saline (vehicle control) or the test substance (anti-IL-16, 1 ug) was injected into the peritoneal cavity just prior to incision closure. Animals were sacrificed at 7 days following surgery. Adhesion formation was quantified in a blinded fashion with each animal receiving a score based on the percentage of ischemic buttons with attached adhesions at 7 days.

Figure 2:
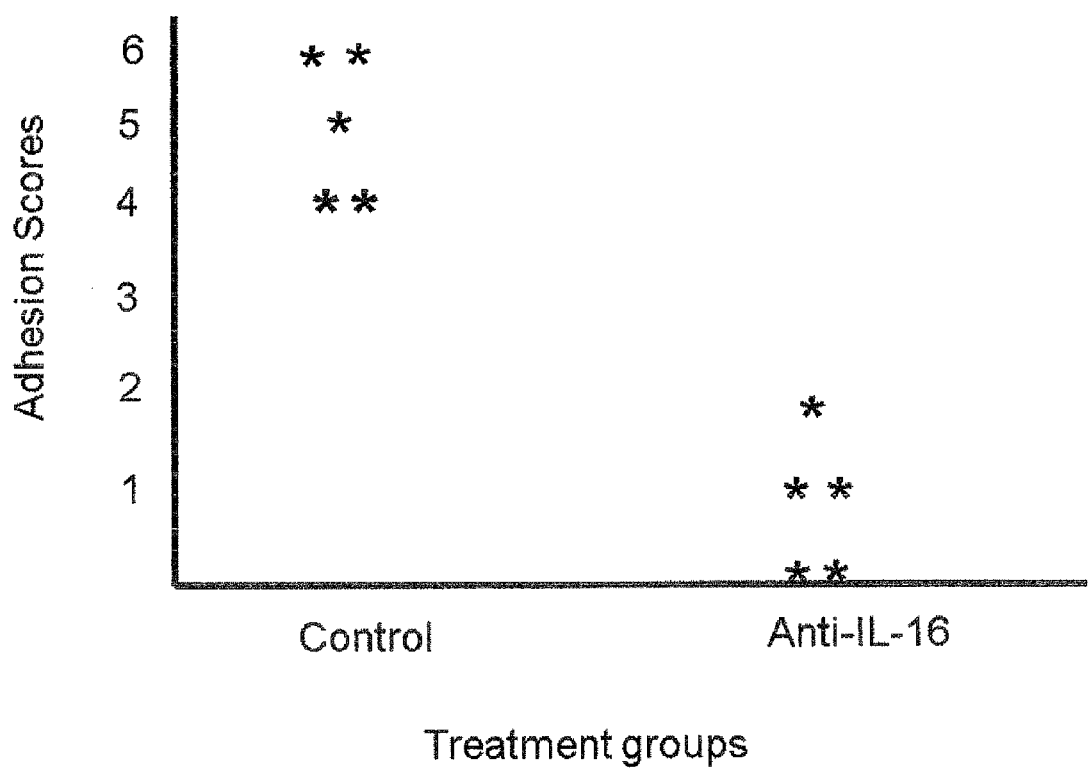
FIG. 2. Male Wistar rats were subjected to cecal abrasion surgery and treated with either anti-IL-16 or control antibody. Animals were sacrificed at 7 days following surgery and adhesion formation was quantified.

Each rat received abrasions (6 per rat) which developed into an abdominal adhesion after 7 days. The adhesions were scored as either present or absent so a maximum of 6 could be reached for each rat. The control rats received control antibody and the anti-IL-16 treated received 1 ug antibody at time of surgery and then at day 3. 4 rats per group were used. The results were shown in FIG. 2.

What is claimed is:

1. A method, comprising administering an IL-16 antagonist to a mammalian subject undergoing surgery to effect at least a reduction in surgery induced adhesion in said subject, wherein said IL-16 antagonist is an anti-IL-16 neutralizing antibody or an antigen-binding fragment thereof, said antibody binds to a peptide fragment of native IL-16 of said subject, and said peptide fragment is of a length of 4-16 amino acids and comprises a RR or KR motif in the C-terminal region of said native IL-16, and wherein said IL-16 antagonist is administered to the subject before, during or not more than 5 days after the surgery.

2. The method of claim 1, wherein said anti-IL-16 antibody is a polyclonal antibody or a monoclonal antibody.

3. The method of claim 1, wherein said anti-IL-16 antibody is a human or humanized antibody.

4. The method of claim 1, where said peptide fragment comprises a sequence selected from the group consisting of: RRKS (SEQ ID NO: 3), VIRR (SEQ ID NO: 9), IRRK (SEQ ID NO: 12), RRKSLQ (SEQ ID NO: 16), RRKSLQSK (SEQ ID NO: 23), and RRKSLQSKETTAAGDS (SEQ ID NO: 32).

5. The method of claim 1, wherein said IL-16 antagonist is administered in combination with another adhesion-preventive agent or a barrier material.

6. The method of claim 5, wherein said IL-16 antagonist has been incorporated into or on said barrier material prior to administration.

7. The method of claim 1, wherein the administration is performed at least during the surgery.

8. The method of claim 1, wherein the mammalian subject is human.

9. The method of claim 1, wherein the administration is performed during and after the surgery.

* * * * *

SEQUENCE LISTING

<160> NUMBER OF SEQ ID NOS: 37

<210> SEQ ID NO 1
<211> LENGTH: 121
<212> TYPE: PRT
<213> ORGANISM: Homo sapiens

<400> SEQUENCE: 1

Ser Ala Ala Ser Ala Ser Ala Ala Ser Asp Val Ser Val Glu Ser Thr
1               5                   10                  15

Ala Glu Ala Thr Val Cys Thr Val Thr Leu Glu Lys Met Ser Ala Gly
            20                  25                  30

Leu Gly Phe Ser Leu Glu Gly Gly Lys Gly Ser Leu His Gly Asp Lys
        35                  40                  45

Pro Leu Thr Ile Asn Arg Ile Phe Lys Gly Ala Ala Ser Glu Gln Ser
    50                  55                  60

Glu Thr Val Gln Pro Gly Asp Glu Ile Leu Gln Leu Gly Thr Ala
65                  70                  75                  80

Met Gln Gly Leu Thr Arg Phe Glu Ala Trp Asn Ile Ile Lys Ala Leu
            85                  90                  95

Pro Asp Gly Pro Val Thr Ile Val Ile Arg Arg Lys Ser Leu Gln Ser
            100                 105                 110

Lys Glu Thr Thr Ala Ala Gly Asp Ser
            115                 120

<210> SEQ ID NO 2
<211> LENGTH: 118
<212> TYPE: PRT
<213> ORGANISM: Mus musculus

<400> SEQUENCE: 2

Ser Ala Ala Ser Ala Ser Ala Ala Ser Asp Ile Ser Val Glu Ser Lys
1               5                   10                  15

Glu Ala Thr Val Cys Thr Val Thr Leu Glu Lys Thr Ser Ala Gly Leu
            20                  25                  30

Gly Phe Ser Leu Glu Gly Gly Lys Gly Ser Leu His Gly Asp Lys Pro
        35                  40                  45

Leu Thr Ile Asn Arg Ile Phe Lys Gly Asp Arg Thr Gly Glu Met Val
    50                  55                  60

Gln Pro Gly Asp Glu Ile Leu Gln Leu Ala Gly Thr Ala Val Gln Gly
65                  70                  75                  80

Leu Thr Arg Phe Glu Ala Trp Asn Val Ile Lys Ala Leu Pro Asp Gly
            85                  90                  95

Pro Val Thr Ile Val Ile Arg Arg Thr Ser Leu Gln Cys Lys Gln Thr
            100                 105                 110

Thr Ala Ser Ala Asp Ser
        115

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 3

Arg Arg Lys Ser
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:Synthetic

```
                    Peptide

<400> SEQUENCE: 4

Arg Arg Thr Ser
  1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 5

Lys Arg Lys Ser
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 6

Arg Arg Ala Ser
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 7

Arg Arg Lys Ala
  1

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 8

Arg Arg Thr Ala
  1

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 9

Val Ile Arg Arg
  1

<210> SEQ ID NO 10
<211> LENGTH: 4
```

```
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 10

Val Leu Arg Arg
  1

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 11

Val Ile Lys Arg
  1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 12

Ile Arg Arg Lys
  1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 13

Ile Arg Arg Thr
  1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 14

Leu Arg Arg Lys
  1

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 15

Ile Lys Arg Lys
  1
```

```
<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 16

Arg Arg Lys Ser Leu Gln
  1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 17

Arg Arg Thr Ser Leu Gln
  1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 18

Arg Arg Lys Ser Cys Met
  1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 19

Lys Arg Lys Ser Met Gln
  1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 20

Arg Arg Ala Ser Leu Gln
  1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide
```

```
<400> SEQUENCE: 21

Arg Arg Lys Ala Leu Gln
  1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 22

Arg Arg Thr Ala Leu Gln
  1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 23

Arg Arg Lys Ser Leu Gln Ser Lys
  1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 24

Arg Arg Thr Ser Leu Gln Cys Lys
  1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 25

Arg Arg Lys Ser Leu Gln Pro Lys
  1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 26

Arg Arg Lys Ser Cys Met Ser Lys
  1               5

<210> SEQ ID NO 27
<211> LENGTH: 8
<212> TYPE: PRT
<213> ORGANISM: Artificial Sequence
```

```
<220> FEATURE:
<223> OTHER INFORMATION: Description of Artificial Sequence:Synthetic
      Peptide

<400> SEQUENCE: 27

Lys Arg Lys Ser Met Gln Ser Lys
  1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 28

Arg Arg Ala Ser Leu Gln Ser Lys
  1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 29

Arg Arg Lys Ala Leu Gln Ser Lys
  1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 30

Arg Arg Thr Ala Leu Gln Cys Lys
  1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 31

Arg Arg Ala Ser Leu Gln Cys Lys
  1               5

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 32

Arg Arg Lys Ser Leu Gln Ser Lys Glu Thr Thr Ala Ala Gly Asp Ser
  1               5                  10                  15
```

```
<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 33

Arg Arg Thr Ser Leu Gln Cys Lys Gln Thr Thr Ala Ser Ala Asp Ser
 1               5                  10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 34

Arg Arg Ala Ser Leu Gln Ser Lys Glu Thr Thr Ala Ala Gly Asp Ser
 1               5                  10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 35

Arg Arg Lys Ala Leu Gln Ser Lys Glu Thr Thr Ala Ala Gly Asp Ser
 1               5                  10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 36

Arg Arg Thr Ala Leu Gln Cys Lys Gln Thr Thr Ala Ser Ala Asp Ser
 1               5                  10                  15

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence:Synthetic
      Peptide

<400> SEQUENCE: 37

Arg Arg Ala Ser Leu Gln Cys Lys Gln Thr Thr Ala Ser Ala Asp Ser
 1               5                  10                  15
```